United States Patent [19]

Rasmusson et al.

[11] 4,220,775
[45] Sep. 2, 1980

[54] PREPARATION OF 4-AZA-17-SUBSTITUTED-5α-ANDROSTAN-3-ONES USEFUL AS 5α-REDUCTASE INHIBITORS

[75] Inventors: Gary H. Rasmusson, Watchung; David B. R. Johnston, Warren; Donald F. Reinhold, North Plainfield; Torleif Utne, Warren; Ronald B. Jobson, East Brunswick, all of N.J.

[73] Assignee: Merck & Co., Inc., Rahway, N.J.

[21] Appl. No.: 20,372

[22] Filed: Mar. 15, 1979

[51] Int. Cl.² .......................................... C07D 221/18
[52] U.S. Cl. .............................. 546/77; 260/239.3 P; 260/397.4; 260/397.1; 260/397.3; 424/263; 424/244; 260/397.5; 549/39
[58] Field of Search .................... 546/77; 260/239.3 P

[56] References Cited

U.S. PATENT DOCUMENTS

| | | | |
|---|---|---|---|
| 2,227,876 | 1/1941 | Bolt | 546/77 |
| 2,897,202 | 7/1959 | Wildi | 546/77 |
| 3,022,312 | 2/1962 | Wildi | 546/77 |
| 3,239,417 | 3/1966 | Di Tullio et al. | 546/77 |
| 3,264,301 | 8/1966 | Doorenbos et al. | 546/77 |
| 3,285,918 | 11/1966 | Doorenbos et al. | 547/77 |

FOREIGN PATENT DOCUMENTS

| | | | |
|---|---|---|---|
| 775919 | 11/1971 | Belgium | 546/77 |
| 970692 | 7/1975 | Canada | 547/77 |
| 1465544 | 12/1966 | France | 546/77 |

OTHER PUBLICATIONS

Doorenbos and Brown, "J. Pharm. Science," vol. 60, No. 8, pp. 1234–1235, (1971).
Doorenbos and Solomon, "J. Pharm. Science," vol. 62, No. 4, pp. 638–640, (1973).
Neri et al., "Endo," vol. 91, No. 2, pp. 429–437, (1972).
Nayfeh et al., "Steroids," vol. 14, pp. 269–283, (1969).

*Primary Examiner*—John M. Ford
*Assistant Examiner*—Robert T. Bond
*Attorney, Agent, or Firm*—Raymond M. Speer; Mario A. Monaco

[57] ABSTRACT

A method of preparing a compound of the formula:

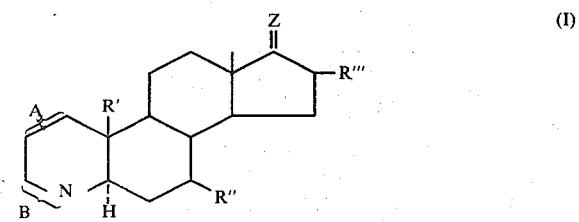

(I)

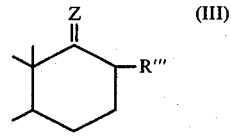

(III)

where Formula (I) may also have the structure of partial Formula (III);

wherein,

A is (1) $-CH_2-CH_2-$;

(2) $-CH=CH-$;

(3) $-\underset{\underset{1}{|}}{\overset{CH_3}{\underset{|}{C}}}-CH_2-$; or (4) $-\underset{1}{CH}\underset{}{\overset{CH_2}{\diagup\diagdown}}\underset{2}{CH}-$ B is (1)

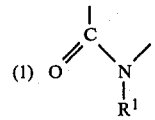

R' is hydrogen or methyl;
R" is hydrogen or β-methyl;
R'" is β-methyl or hydroxy;
Z is (1) oxo;
  (2) β-hydrogen and α-hydroxy; or α-hydrogen or α-hydroxyl and
  (3) $(Y)_n Q$ where n=0 or 1, Y is a straight or branched hydrocarbon chain of 1 to 12 carbon atoms and
  Q is

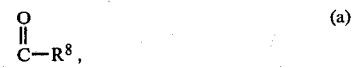

(a)

where $R^8$ is,

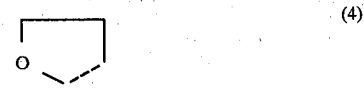

(4)

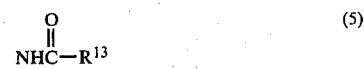

(5)

where the dashed bond replaces the 17α hydrogen;
  (6) cyano; or
  (7) tetrazolyl;

and pharmaceutically acceptable salts of the above compounds;

CHARACTERIZED IN THAT (I.) a compound of the formula:

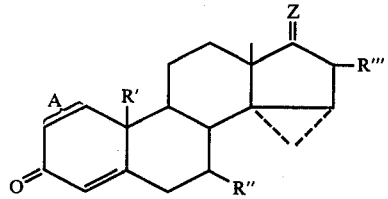

, where A has the meanings above except —CH=CH—, is (1) treated with an oxidizing agent at reduced temperatures to form the corresponding 5-oxo-3,5-seco-androstan-3-oic acid compound;

(2) treating the product of step (1) with an amine of formula: $R^1NH_2$ to form the corresponding 4-aza-5-androsten-3-one compound substituted in the 4-position with $R^1$; and (3) treating the product of step (2) with hydrogen under catalytic conditions to form the compound of Formula I and I & II wherein B is

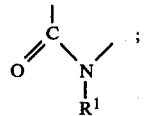

(II.) and where it is desired to prepare compounds of Formula I wherein B is

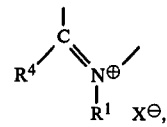

additionally carrying out the following steps on the products prepared by the procedures in (I.) above:

(1) alkylating the lactim carbonyl by treating it with trialkyloxonium tetrafluoroborate to form the corresponding alkyl iminium ether, i.e., the compound of Formula I where B is as above and $R^4=OR^5$;

(2) treating the product of step (1) with an amine of formula $HNR^6R^7$ followed by treatment with a mineral acid to form the compound of Formula I where B is as above and $R^4=NR^6R^7$;

(III.) and where it is desired to prepare compounds of Formula I wherein A is —CH=CH—, additionally carrying out the following steps on the products prepared by the procedures in (I.) above:

(1) treating the 1,2 saturated compound with lithium diisopropyl amide to form the corresponding enolate;

(2) treating the enolate of step (1) in situ with diphenyldisulfide to form the corresponding α-phenylthio compound;

(3) oxidizing the product of step (2) to form the corresponding sulfoxide compound; and (4) heating the product of step (3) to form the compound of Formula I wherein A is —CH=CH—.

2 Claims, No Drawings

PREPARATION OF 4-AZA-17-SUBSTITUTED-5α-ANDROSTAN-3-ONES USEFUL AS 5α-REDUCTASE INHIBITORS

BACKGROUND OF THE INVENTION

1. Field of the Invention

The present invention is concerned with methods for preparing novel 4-aza-17-substituted-5α-androstan-3-ones and their A- and D- homo analogs, useful as testosterone 5α-reductase inhibitors.

2. Description of the Prior Art

It is well known in the art that certain undesirable physiological manifestations, such as acne vulgaris, seborrhea, female hirsutism, and male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testosterone-5α-reductase will serve to prevent or lessen symptoms of hyperandrogenic stimulation. Nayfeh et al., Steroids, 14, 269 (1969) demonstrated in vitro that methyl 4-androsten-3-one-17β-carboxylate was a testosterone-5α-reductase inhibitor. Then Voigt and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotestosterone caused enlargement of the female hamster flank organ, an androgen dependent sebaceous structure. However, concommitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

The novel compounds prepared by the methods of the present invention are, therefore, potent antiandrogens by virtue of their ability to specifically inhibit testosterone-5α-reductase.

Heretofore, it has not been known to use 4-aza-17-substituted-5α-androstan-3-ones for treating hyperandrogenic conditions, although Selye, in Belgian Pat. No. 775,919, describes such a compound, and a number of other compounds, additionally having one or more carbonitrile substituents, as a catatoxic agent useful in the treatment of, among other conditions, prostatic hypertrophy.

A number of 4-azo steroid compounds are known. See, for example, U.S. Pat. Nos. 2,227,876; 3,239,417; 3,264,301; and 3,285,918; French Pat. No. 1,465,544; Doorenbos and Solomons, *J. Phar. Sci.* 62, 4, pp. 638–640 (1973) and Doorenbos and Brown, *J. Pharm. Sci.*, 60, 8, pp. 1234–1235 (1971). However, none of the known compounds suggest the 4-aza compounds of the present invention or their use in treating hyperandrogenic conditions.

SUMMARY OF THE INVENTION

The present invention is concerned with processes for preparing novel antiandrogenic 4-aza-17-substituted-5α-androstan-3-ones, their A- and D- homo analogs, and certain isosteres and derivatives thereof.

The present invention is particularly concerned with preparing novel compounds of the formula:

(I)  (II)  (III)

where Formula (I) may also have the structure of partial Formulas (II) and/or (III); wherein, A is $-CH_2-CH_2-$; (1)

$-CH=CH-$; (2)

$$\begin{array}{c} CH_3 \\ | \\ -C-CH_2-; \text{ or} \\ | \\ 1 \quad 2 \end{array}$$ (3)

$$\begin{array}{c} CH_2 \\ / \quad \backslash \\ -CH-\!\!-\!\!-CH- \end{array}$$ (4)

B is (1)

$$\begin{array}{c} | \\ C \\ // \quad \backslash \quad / \\ O \quad N \\ | \\ R^1 \end{array}$$

-continued where $R^1$ is,
(a) hydrogen;
(b) methyl or ethyl;
(c) ethenyl;
(d) ethynyl;
(e) $NR^2R^3$ where $R^2$ and $R^3$ are hydrogen or methyl;
(f) cyano; or (2) 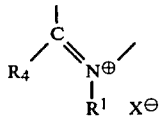

where $X^\ominus$ is any anion and $R^4$ is,
(a) $OR^5$ where $R^5$ is $C_{1-4}$ alkyl; or
(b) $NR^6R^7$, where $R^6$ and $R^7$ are hydrogen or methyl;

$R'$ is hydrogen or methyl;
$R''$ is hydrogen or $\beta$-methyl;
$R'''$ is $\beta$-methyl or hydroxy;
Z is (1) oxo;
(2) $\beta$-hydrogen and $\alpha$-hydroxy; or $\alpha$-hydrogen or $\alpha$-hydroxyl and
(3) $(Y)_n$ Q where n=0 or 1, Y is a straight or branched hydrocarbon chain of 1 to 12 carbon atoms and Q is (a) 

where $R^8$ is,
(i) hydrogen,
(ii) hydroxyl,
(iii) $C_{1-4}$ alkyl
(iv) $NR^9R^{10}$, where $R^9$ and $R^{10}$ are each independently selected from hydrogen, $C_{1-4}$ straight or branched chain alkyl, $C_{3-6}$ cycloalkyl, phenyl; or $R^9$ and $R^{10}$ taken together with the nitrogen to which they are attached represent a 5-6 membered saturated ring comprising up to one other heteratom selected from oxygen and nitrogen.
(v) $OR^{11}$, where $R^{11}$ is M, where M is hydrogen or alkali metal, or $C_{1-18}$ straight or branched chain alkyl; benzyl; or
(b) $OR^{12}$, provided that for 17α—OH, n must=1, where $R^{12}$ is,
(i) $C_{1-20}$ alkylcarbonyl,
(ii) phenyl $C_{1-16}$ alkylcarbonyl,
(iii) $C_{5-10}$ cycloalkylcarbonyl,
(iv) benzoyl, or
(v) $C_{1-8}$ alkoxycarbonyl;
(4)

, where the dashed bond replaces the 17α hydrogen;
(5)

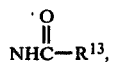

provided that for 17α—OH, n must=1, where $R^{13}$ is,
(a) $C_{1-12}$ alkyl; or
(b) $NR^9R^{10}$;
(6) cyano; or
(7) tetrazolyl;

and pharmaceutically acceptable salts of the above compounds.

Unless otherwise indicated, both the α and β stero configurations for various substituents are intended.

Representative compounds prepared by the methods of the present invention are, among others, the following:

17β-N,N-diethylcarbamoyl-4-methyl-4-aza-5α-androstan-3-one
17β-N,N-diethylcarbamoyl-4-aza-5α-androstan-3-one
17β-N,N-diethylcarbamoyl-4-amino-4-aza-5α-androstan-3-one
17β-acetoxy-4-aza-5α-androstan-3-one
4-aza-20-spirox-5α-an-3-one
4-methyl-4-aa-5α-20-spiroxan-3-one
17β-N-ethylcarbamoyl-4-methyl-4-aza-5α-androst-3-one
4-ethyl-4-aza-5α-20-spiroxan-3-one
17β-carbomethoxy-4-methyl-4-aza-5α-androstan-3-one The novel compounds of Formula I and of Formula I having the structure of partial formula III of the present invention may be prepared by a method comprising the following steps:

a compound of the formula:

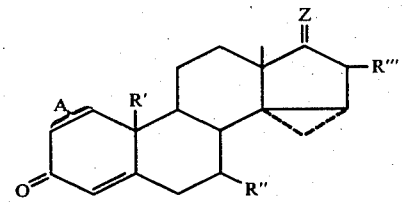

where A has the meanings above except, —CH=CH—, is (1) treated with an oxidizing agent at reduced temperatures to form the corresponding 5-oxo-3,5-secoandrostan-3-oic acid compound;
(2) treating the product of step (1) with an amine of formula: $R^1NH_2$ to form the corresponding 4-aza-5-androsten-3-one compound substituted in the 4-position with $R^1$; and
(3) treating the product of step (2) with hydrogen under catalytic conditions to form the compound of Formula I and I+III wherein B is

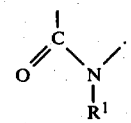

Thus, the last step of this method is an hydrogenation step which introduces the 5α hydrogen. The above reactions are further detailed in Examples 1-8 following, and are schematically represented in the following diagram:

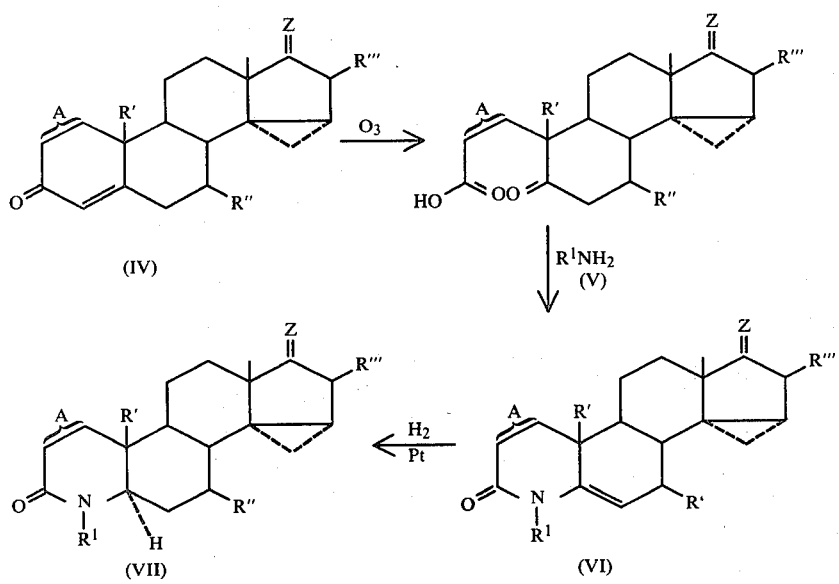

(IV) → (V) R¹NH₂ → (VI) H₂/Pt → (VII)

Where it is desired to prepare compounds of Formula I wherein B is

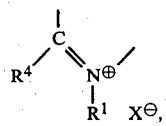

there may be additionally carried out, on the products prepared by the procedures discussed immediately above, the following steps:

(1) Alkylting the lactim carbonyl by treating it with trialkyloxonium tetrafluoroborate to form the corresponding alkyl iminium ether, i.e., the compound of Formula I where B is as above and $R^4=OR^5$. A typical procedure of this type is described in the first portion of Example 11 following.

(2) Treating the product of step (1) with an amine of formula $HNR^6R^7$ followed by treatment with a mineral acid to form the compound of Formula I where B is as above and $R^4=NR^6R^7$. A typical procedure of this type is described in Example 18 following.

Where it is desired to prepare compounds of Formula I wherein A is —CH=CH—, there may be additionally carried out, on the products prepared by the procedures discussed above on pages 6 and 7, the following steps:

(1) treating the 1,2 saturated compound with lithium diisopropyl amide to form the corresponding enolate;

(2) treating the enolate of step (1) in situ with diphenyldisulfide to form the corresponding α-phenylthio compound;

(3) oxidizing the product of step (2) to form the corresponding sulfoxide compound; and (4) heating the product of step (3) to form the compound of Formula I wherein A is —CH=CH—. A typical procedure of this type is described in Example 10 following.

A preferred process for preparing 17β-N,N-diethylcarbamoyl-4-methyl-4-aza-5α-androstan-3-one, an especially preferred compound of the present invention, comprises the following steps: (a) pregnenolone (V), an available starting material, is treated by the haloform King reaction with iodine and pyridine to form the 20-pyridinum iodide derivative of the pregnenolone (VI); (b) the pyridinium iodide derivative (VI) is methanolyzed to the methyl ester of 17-carboxy androstenol (VII) with sodium methoxide and methanol, the ester form being preferred for carrying out the following Oppenhauer reaction; (c) the methyl ester of 17-carboxy androstenol (VII) is treated with aluminum isopropoxide and cyclohexanone in an appropriate solvent such as toluene to yield methyl-4-androstene-3-one-17-carboxylate (VIII) (d) the methyl-4-androstene-3-one-17-carboxylate (VIII) thus formed is hydrolyzed to the 17-acid (IX) under acid conditions in a methanol: water solvent of approximately 4:1 proportions; (e) the 17 acid (IX) is then treated with an oxalyl chloride: pyridine complex of approximately 1:1 proportions in toluene or other suitable solvent, e.g. xylene, to form the 17-acid chloride (X); (f) the 17-acid chloride (X) is then treated in situ with an excess of diethylamine to form the 17β-N,N-diethylcarbamoyl-4-androstene-3-one (XI); (g) the 4-androstene-3-one (XI) thus formed is oxidized by treatment with sodium periodate and potassium permanganate, using tert-butanol and water as a solvent system, to the corresponding 5-oxo-3,5-secoandrostan-3-oic acid (XII); (h) the secoandrostanoic acid (XII) is then converted to the corresponding 4-aza compound (XIII) by treating it with methylamine in ethylene glycol for a period of about 1 hour over which time the reaction mixture temperature is raised to from 140°–180° C. where it is maintained from 0.5 to 5 minutes; (i) the resulting 17β-N,N-diethylcarbamoyl-4-methyl-4-aza-5-androsten-3-one (XIII) is then hydrogenated by treating it with hydrogen at room temperature to 60° C. or higher, using platinum oxide as the catalyst, to form the 17β-N,N-diethylcarbamoyl-4-methyl-4-aza-5α-androstan-3-one (XIV) final product, which is then separated and purified.

The above reactions are further detailed in Example 20 following, and are schematically represented in the following diagram:

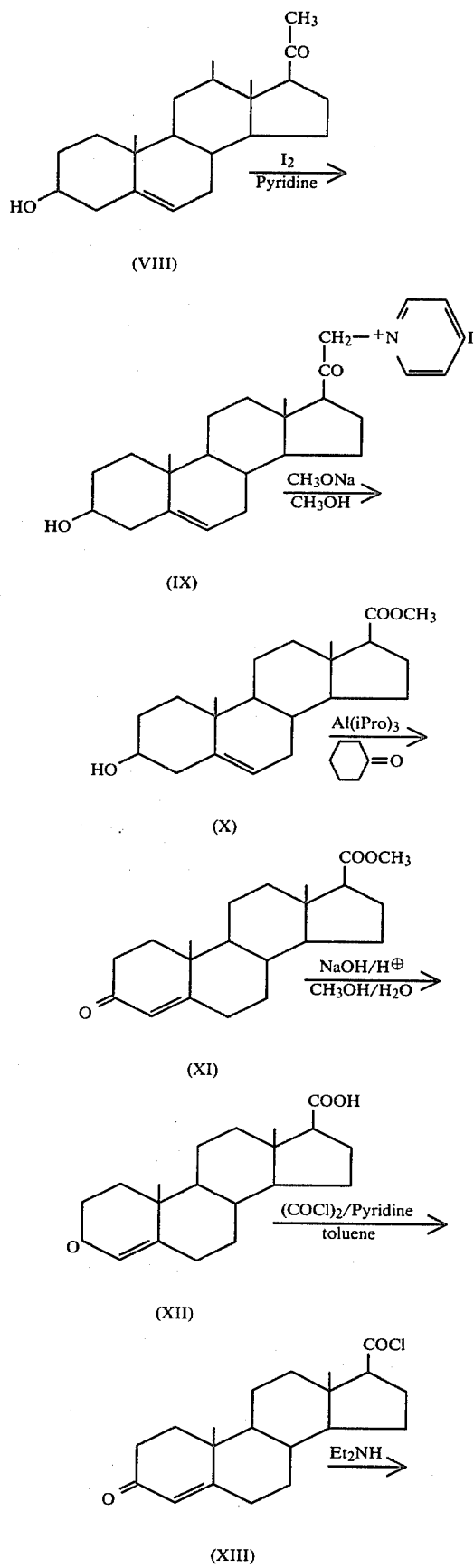

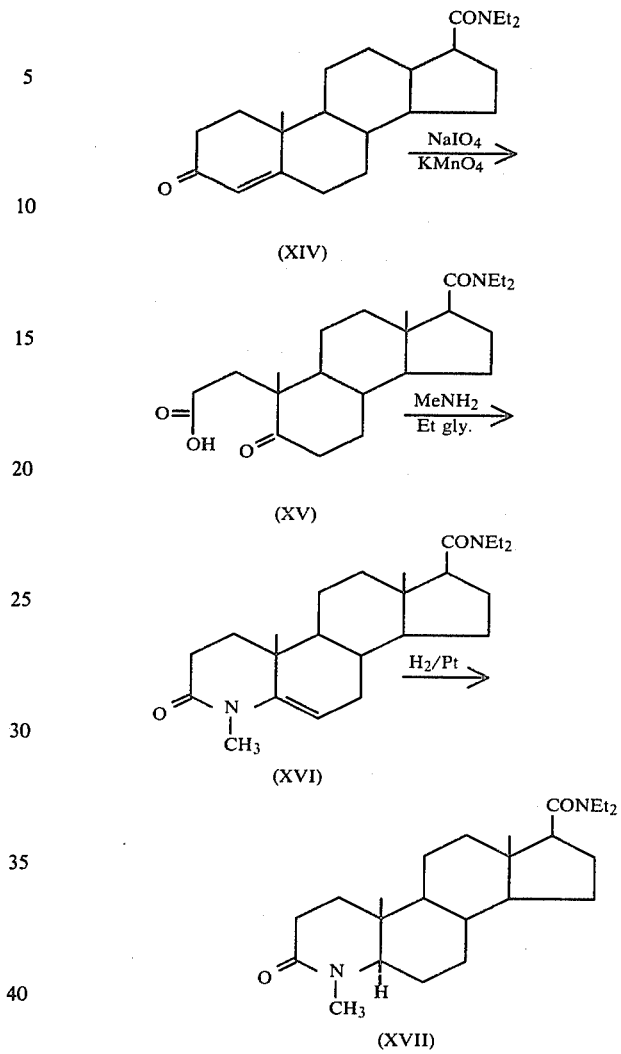

The novel compounds of Formula I of the present invention may also be prepared by a method whose last step substitutes the nitrogen atom of the A-ring with a methyl group, comprising the steps of (1) treating a 5-oxo-3,5-secoandrostan-3-oic acid compound with ammonia to form the corresponding 4-aza-5-androsten-3-one compound; (2) hydrogenating the product of step (1) by treating it with hydrogen under catalytic conditions to form the 4-aza-5α-androstan-3-one compound; and (3) treating the product of step (2) with a methylating agent, e.g., sodium hydride and methyl iodide, to form the 4-methyl-4-aza-5α-androstan-3-one final product.

The above method is suitable for preparing 17β-N,N-diethylcarbamoyl-4-methyl-4-aza-5α-androstan-3-one, an especially preferred compound of the present invention, for which the starting material is 17β-N,N-diethylcarbamoyl-5-oxo-3,5-secoandrostan-3-oic acid.

The above reactions are further detailed in Example 12 following, and are schematically represented in the following diagram:

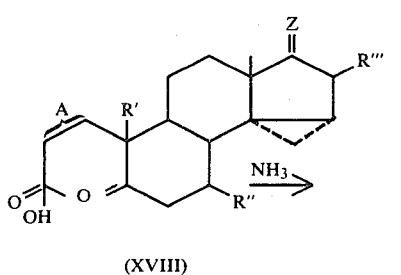

(XVIII)

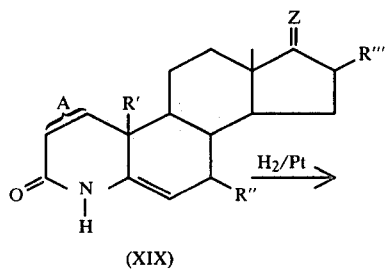

(XIX)

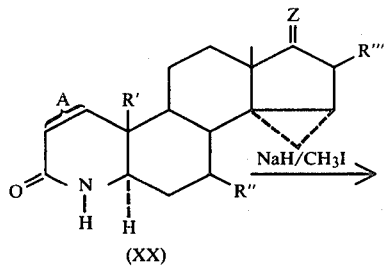

(XX)

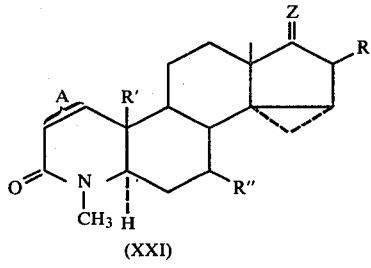

(XXI)

The novel compounds of Formula I of the present invention may also be prepared by a method whose last step is ring closure to form the nitrogen-containing A-ring, comprising the steps of (1) treating a 5-oxo-3,5-secoandrostan-3-oic acid compound with methylamine to form the corresponding 5-methylamine-3,5-secoandrostan-3-oic acid compound; and (2) reducing, in situ and under catalytic conditions, the product of step (1) to form the 4-methyl-4-aza-5α-androstan-3-one final product.

The above method is suitable for preparing 17β-N,N-diethylcarbamoyl-4-methyl-4-aza-5α-androstan-3-one, an especially preferred compound of the present invention, for which the starting material is 17β-N,N-diethylcarbamoyl-5-oxo-3,5-secoandrostan-3-oic acid.

The above reactions are further detailed in Example 13 following, and are schematically represented in the following diagram:

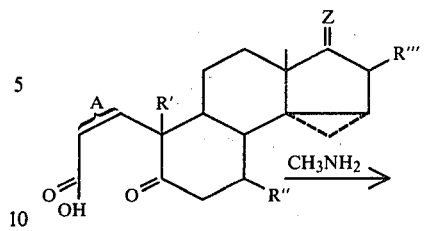

(XXII)

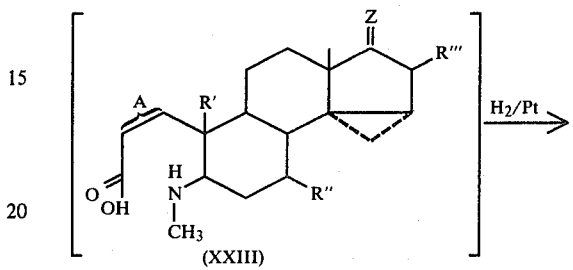

(XXIII)

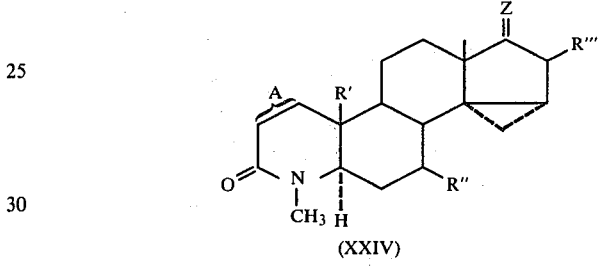

(XXIV)

The especially preferred compound, 17β-N,N-diethylcarbamoyl-4-methyl-4-aza-5αandrostan-3-one, may be prepared by a method whose last step is addition of the 17β-position diethylamide side chain, comprising the steps of (1) treating 17β-carboxy-4-androsten-3-one with an oxidizing agent, e.g., sodium metaperiodate, to form 5-oxo-3,5-secoandrostan-3,17β-dioic acid; (2) treating the product of step (1) with methylamine to form 17β-carboxy-4-methyl-4-aza-5-androsten-3-one; (3) hydrogenating the product of step (2) under catalytic conditions to form 17β-carboxy-4-methyl-4-aza-5α-androsten-3-one; (4) forming the sodium salt of the product of step (3) and treating it with oxalyl chloride to form 17β-carbonylchloro-4-methyl-4-aza-5α-androstan-3-one; and (5) treating the product of step (4) with diethylamine to form 17β-N,N-diethylcarbamoyl-4-methyl-4-aza-5α-androstan-3-one.

The above reactions are further detailed in Example 14 following, and are schematically represented in the following diagram:

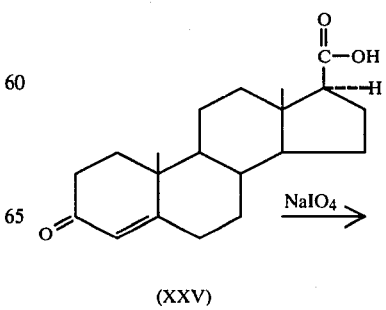

(XXV)

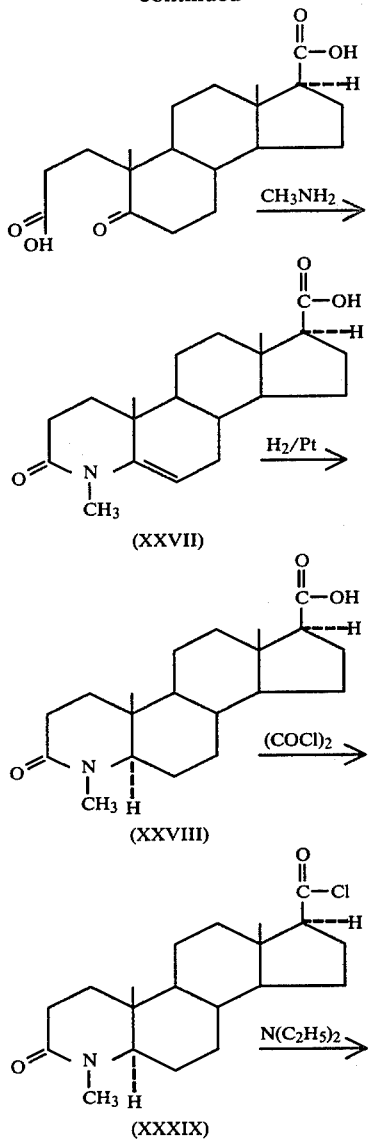

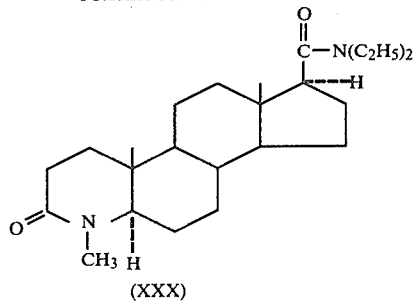

The especially preferred compound, 17β-N,N-diethylcarbamoyl-4-methyl-4-aza-5α-androstan-3-one, may also be prepared by a method whose last step is diethylation of the corresponding 17β-carbamoyl compound, or by a method whose last step is monethylation of the corresponding 17β-N-ethylcarbamoyl compound. These two methods comprise the following steps:

(1) treating 17β-carboxy-4-methyl-4-aza-5α-androstan-3-one with oxalyl chloride to form 17β-carbonyl chloro-4-methyl-4-aza-5α-androstan-3-one;

(2) treating the product of step (1) with ammonia to form 17β-carbamoyl-4-methyl-4-aza-5α-androstan-3-one; and (3) treating the product of step (2) with an ethylating agent such as ethyl bromide or diethyl sulfate in the presence of equimolar amounts of sodium hydride or sodium methylate, respectively, to form the desired final product; alternatively, (2a) treating the product of step (1) with monoethylamine to form the corresponding 17β-N-ethylcarbamoyl compound; and (3a) treating the product of step (2a) with a monoethylating agent such as ethyl bromide and sodium hydride to form the desired final product.

The above reactions are further detailed in Examples 16 and 17 following, and are schematically represented in the following diagram:

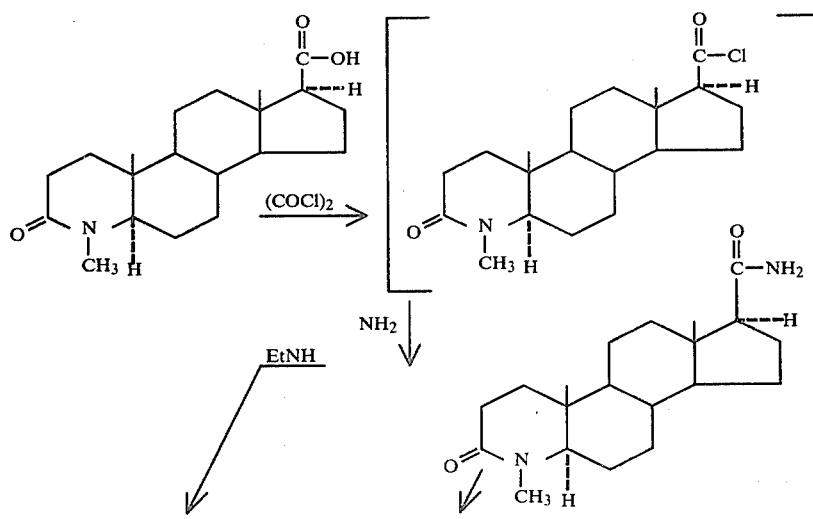

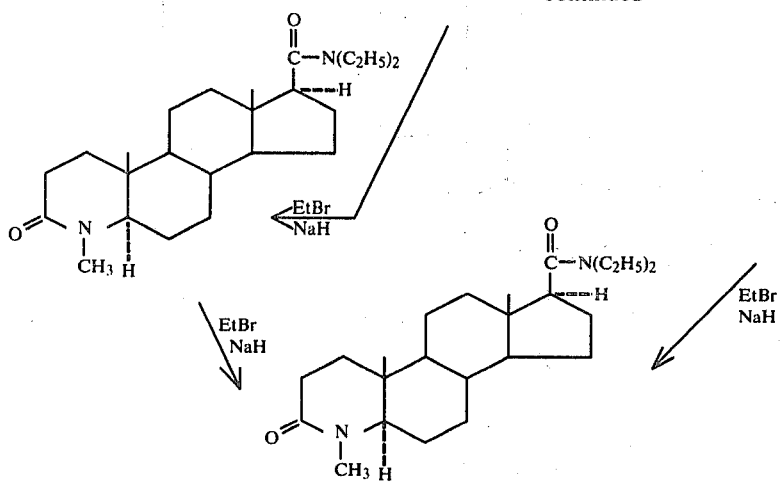

The novel compounds of Formula I which incorporate the structure of partial Formula II of the present invention, i.e., the A-homo analogs, may be prepared by a method comprising the steps of (1) reacting a testosterone with ethanedithiol in the presence of boron trifluoride etherate to form a 3-dithioketal derivative of the testosterone; (2) reacting the product of step (1) with sodium and liquid ammonia to remove the 3-dithioketal substituent; (3) reacting the product of step (2) with dihydropyran in the presence of p-toluene-sulfonyl chloride to form a 17-tetrahydropyranyloxy derivative; (4) reacting the product of step (3) with borane and then with sodium hydroxide and hydrogen peroxide to form a 4-hydroxy-5α-hydrogen compound; (5) reacting the product of step (4) with chromium trioxide to form a 4-keto compound; (6) treating the product of step (5) with acid to remove the 17-tetrahydropyranyl protective group and form a 17-hydroxy compound; (7) reacting the product of step (6) with acetic anhydride to form a 17-acetoxy compound; (8) reacting the product of step (7) with hydroxylamine hydrochloride to form a 4-oxime compound; and (9) reacting the product of Step (8) with thionyl chloride and then potassium hydroxide to form a compound of Formula I which incorporates the structure of partial Formula II, an A-homo-4α-aza compound.

The above reactions are further detailed in Example 9 following, and are schematically represented in the following diagram:

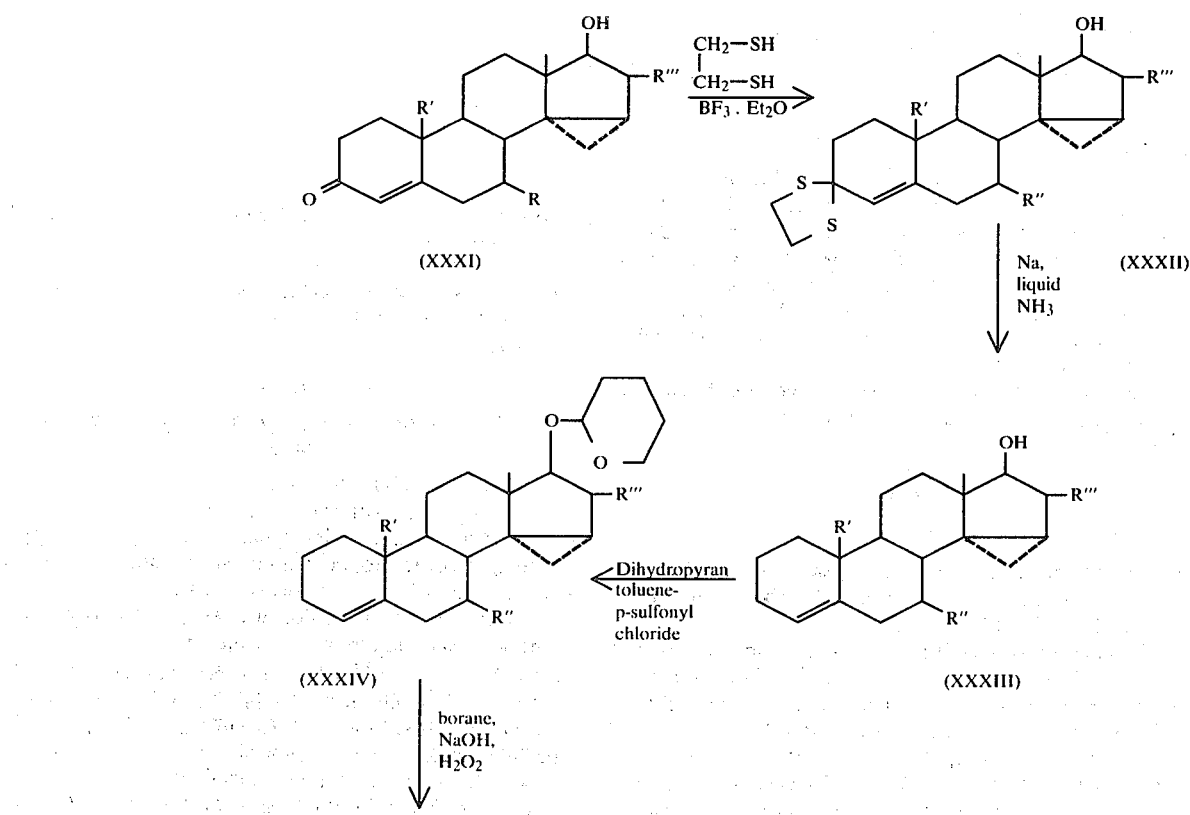

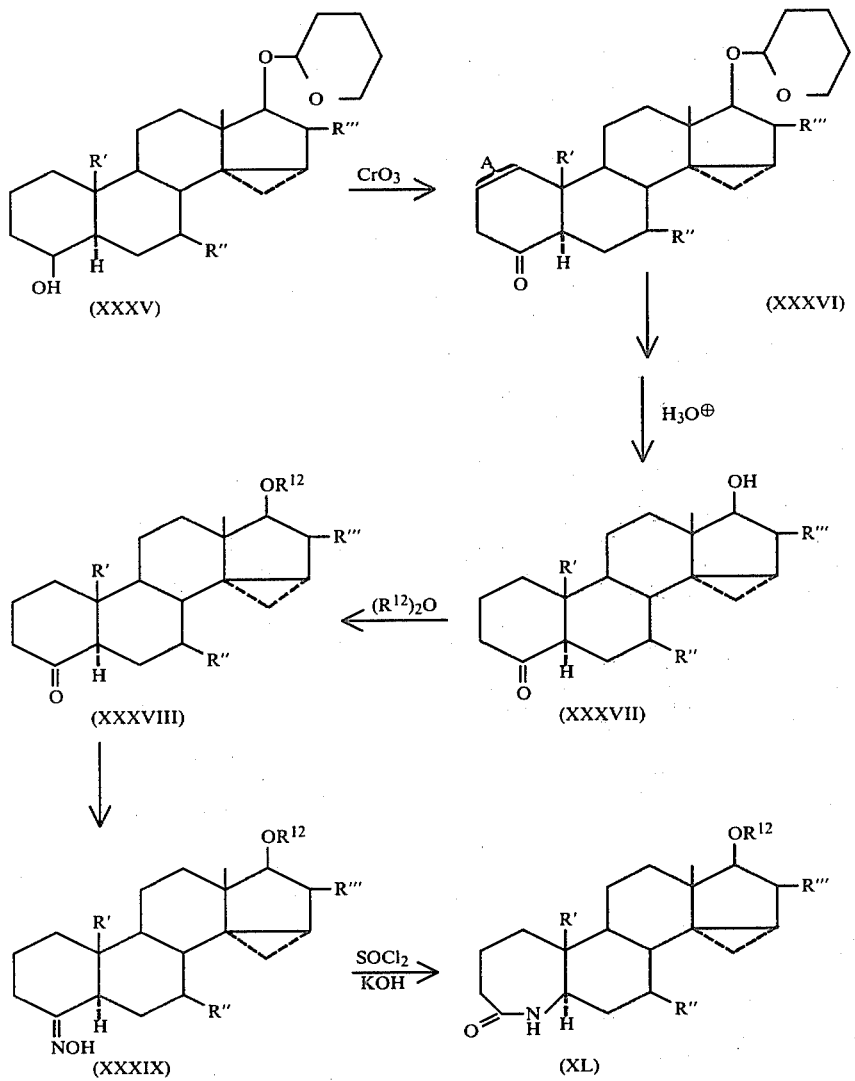

The novel compounds of Formula I which incorporate the structure of partial Formula III of the present invention, i.e., the D-homo analogs, may be prepared by a number of different methods known in the art, including those described in *J. Steroid Biochem.*, Vol. 5, No. 4, p. 298 (June 1974) by Alig et al. and Kerb et al., and in *Helv. Chim. Acta*, Vol. 23, pp. 376–384 and 840–845 by Goldberg and Mannier.

Novel compounds of the present invention having a 1,2α-methylene substituent, i.e. where A is

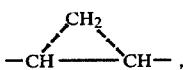

may be prepared in accordance with methods known in the art, including, e.g., that described in Chem. and Ind., p. 1710 (Oct. 10, 1964) by Loev et al.

Novel compounds of the present invention which are Δ 1, i.e. where A is —CH =CH, and in which the 4-nitrogen carries a substituent other than hydrogen, may be prepared in accordance with the procedures described in Example 10 which follows. Where the 4-nitrogen is substituted only with hydrogen, the novel compounds of the present invention may be prepared in accordance with the procedures described in Example 11 following.

The methods of preparing the novel compounds of the present invention, already described above in general terms, may be further illustrated by the following examples:

EXAMPLE 1

17β-N,N-diethylcarbamoyl-4-methyl-4-aza-5α-androstan-3-one

A. 3-oxo-N,N-diethyl-4-etienamide

Twenty grams of sodium 3-oxo-4-etienate was suspended in 360 ml. of dry benzene and 0.13 ml. of pyridine and cooled to 14° C. The suspension was treated with 20 ml. of oxalyl chloride and stirred at 15° C. for 15–20 min. The suspension was evaporated to dryness and then slurried up, as a suspension, in 125 ml. of dry tetrahydrofuran. This suspension was then added to a solution of 25 ml. of diethylamine in 125 ml. of tetrahydrofuran and stirred at room temperature for 1 hr., after which the mixture was poured into 4 l. of ice water. A semi-crystalline precipitate resulted which was extracted with ethyl acetate, washed with water and then saturated brine, and dried and evaporated to 25.7 g. of product. The product was recrystallized from ethyl ether; the first crop of 10.0 g. had a m.p. of 127°–129° C. and the second crop of 3.1 g. had a m.p. of 114°–119° C.

B. 17β-N,N-diethylcarbamoyl-5-oxo-3,5-secoandrostan-3-oic acid

Fifteen grams of the product of Step A. was dissolved in 150 ml. of dichloromethane and 75 ml. of methanol and cooled to −78° C., after which ozone was bubbled through the solution until a blue color persisted. The reaction solution was then warmed to room temperature and purged with nitrogen, after which it was evaporated to dryness at 35° C. The residue was dissolved in benzene and extracted three times with 2.5 N NaOH. These basic washes were combined and acidified with concentrated HCl, extracted with benzene, washed, dried, and evaporated to 11.5 g. of a white crystalline solid. The product was recrystallized from ethyl acetate and found to have a m.p. of 205°–208° C.

C. 17β-N,N-diethylcarbamoyl-4-aza-4-methyl-5-androsten 3-one

To 190 ml. of ethanol was added 26.3 g. of the product of Step B to form a solution. The solution was cooled in an ice bath and saturated with methylamine, and then heated at 180° C. for 8 hrs. the reaction mixture was then cooled to room temperature and evaporated to yield 22.3 g. of a yellowish solid. After chromatographing and recrystallization from ethyl ether, the final product was found to have a m.p. of 120°–122° C.

D. 17β-N,N-diethylcarbamoyl-4-methyl-4-aza-5α-androstan-3-one

To 1 liter of glacial acetic acid was added 36.5 g. of the product of Step C to form a solution. The solution was then treated with 3.5 g. of platinum oxide catalyst and hydrogenated at 40 p.s.i. at room temperature for 8 hrs. The reaction mixture was then filtered and evaporated to dryness. The residue was dissolved in chloroform and washed with a bicarbonate solution, brine, and then dried and evaporated to dryness. The product was recrystallized from ethyl ether to yield 30.65 g. of a white crystalline final product having a m.p. of 168°–170° C.

EXAMPLES 2–8

Following the procedures described in Example 1 above, but substituting for the 3-oxo-4-etienate in Step A an equimolar amount of other available or readily prepared 3-oxo-$\Delta^4$ compounds, or substituting for the diethylamine an equimolar amount of another appropriate amine, there were prepared the compounds of Formula I of the present invention enumerated in the following table.

TABLE

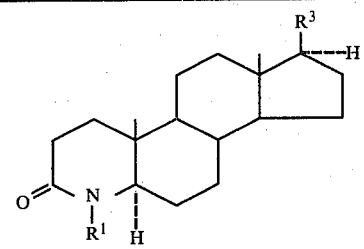

| Example No. | $R^1$ | $R^3$ | m.p. (°C.) |
|---|---|---|---|
| 2 | H | CON(CH$_2$CH$_3$)$_2$ | 263–265 |
| 3 | H | (tetrahydrofuran-2-yl) | 283–285 |
| 4 | CH$_3$ | (tetrahydrofuran-2-yl) | 138–140 |
| 5 | H | COCH$_3$ | 272–275 |
| 6 | CH$_3$ | COCH$_3$ | 218–220 |
| 7 | CH$_3$ | CONHCH$_2$CH$_3$ | 249–251 |
| 8 | H | COOCH$_3$ | 300–302 |

EXAMPLE 9

17β-acetoxy-4a-aza-5α-A-homoandrostan-4-one

A. 17β-hydroxy-4-androstene-3-thioketal

A solution was prepared from 7.5 g. of testosterone, 37.5 ml. of glacial acetic acid, 4.5 ml. of ethanedithiol, and 3.0 ml. of boran trifluoride etherate at 0° C. The mixture was allowed to come to room temperature where it was maintained for 1.5 hrs. The mixture was then diluted with water, extracted with chloroform, and washed with 5% sodium bicarbonate, then water several times, then a saturated sodium chloride solution. The mixture was then dried and evaporated to yield a white solid which was recrystallized from methanol to give 9.0 g. of final product (95% yield) having a m.p. of 160°–162° C.

B. 17β-hydroxy-4-androstene

To 60 ml. of anhydrous liquid ammonia was added 1.2 g. of metallic sodium. To this solution was added 1.0 g. of the thioketal in 10 ml. of dry tetrahydrofuran and the solution was refluxed for 20 min. The solution as quenched with a few ml. of ethanol and evaporated at room temperature. The solution was then diluted with water, extracted with dichloromethane, washed with water, HCl, then water, and dried and evaporated to a white solid having a m.p. of 149°–152° C. (609 mg., 81% yield).

C. 17β-tetrahydropyranyloxy-4-androstene

To 30 ml. of dihdropyran containing 450 mg. of p-toluenesulfonyl chloride was added 6.0 g. of the product of Step B and the solution was stirred at room temperature for 1 hr. The solution was then diluted with ethyl ether and washed with a 20% pyridine water mixture twice, and then water, then brine, and dried and evaporated to yield a pale yellow oil which crystallized (8.5 g.), and had a m.p. of 92°–96° C.

D. 17β-tetrahydropyranyloxy-4β-hydroxy-5α-androstane

To a cooled solution (0° C.) of 5 ml. of 1 M borane in tetrahydrofuran in 2.7 ml. of dry tetrahydrofuran was added 500 mg. (1.4 millimole) of the product of Step C. in 2.0 ml. of dry tetrahydrofuran. The clear solution was stirred for 1 hr. at room temperature and then cooled to 0° C. and treated with 5 ml. of 2.5 N sodium hydroxide followed by 4 ml. of 30% hydrogen peroxide. The solution was stirred for 1 hr. at room temperature, diluted with water and extracted with ethyl ether, washed with water, brine, dried and evaporated to an oily crystalline material. The product was washed with cold methanol and pumped dry to give 175 mg. of final product having a m.p. of 167°–170° C.

E. 17β-tetrahydropyranyloxy-5α-androstan-4-one

To 0.42 ml. of dry pyridine and 6.3 ml. of dry dichloromethane was slowly added 0.264 g. of chromium trioxide and the mixture was stirred for 15 min. at room temperature. To the mixture was added a solution of 175 mg. of the product of Step D in 0.7 ml. of dichloromethane and the resulting mixture was stirred for 20 min. at room temperature. The mixture was diluted with water, extracted with ethyl ether, and washed with 2.5 N sodium hydroxide, water, and brine. The mixture was then dried and evaporated to a clear oil.

F. 17β-hydroxy-5α-androstan-4-one

To 75 ml. of ethanol was added 2.32 g. of the product of Step E to form a solution which was then treated with 5 ml. of 2.5 N hydrochloric acid and warmed on a steam bath for 40 min. to yield 2.1 g. of a crystalline product having a m.p. of 123°–126° C.

17β-acetoxy-5α-androstan-4-one

To 12 ml. of dry pyridine and 6 ml. of acetic anhydride was added 2.0 g. of the product of Step F to form a solution which was heated on a stem bath for 30 min. and then poured into 175 ml. of ice water and stirred to decompose the excess anhydride. The reaction mixture was filtered, washed with water, and pumped dry under high vacuum at 50° C. to yield 1.7 g. of final product having a m.p. of 160°–163° C.

H. 17β-acetoxy-5α-androstan-4-oxime

To 125 ml. of ethanol and 30 ml. of dry pyridine was added 2.0 g. of the product of Step G to form solution which was treated with 420 mg. of hydroxylamine hydrochloride and stirred at room temperature. The reaction mixture was chromatographed by thin layer chromatography on silica gel in 20% ethylacetate/benzene which was allowed to run overnight. The product was concentrated to low volume at 30°–40° C. under high vacuum and diluted slowly with water to form a white crystalline material which was filtered, washed with water, dissolved in ethyl ether, dried, and recrystallized from ethyl ether. The final product had a m.p. of 222°–224° C.

I. 17β-acetoxy-4a aza-5α-A-homoandrostan-4-one

To 3.3 ml. of distilled thionyl chloride at −78° C. was added 500 mg. of the product of Step H and the resulting solution as stirred for 1–2 min. and then slowly added to 50 ml. of 4 N potassium hydroxide at 20° C. A solid precipitate formed which was filtered and washed well with water and then ethyl ether. The product was recrystallized from ethylacetate, washed with ethylacetate, ethyl ether and dried to yield 210 mg. of final product having a m.p. of 232°–235° C.

EXAMPLE 10

17β-N,N-diethylcarbamoyl-4-methyl-4-aza-5α-androst-1-en-3-one

A solution of 0.20 g. of anhydrous diisopropylamine in 5.0 ml. of anhydrous tetrahydrofuran is treated at −78° C. under nitrogen with 0.9 ml. of 2.2 M butyllithium. After 20 minutes at −78° C., a solution of 388 mg. of 17β-N, N-diethylcarbamoyl-4-methyl-4-aza-5α-androstan-3-one in 3 ml. of tetrahydrofuran is added dropwise to the reaction mixture. After stirring at −78° C. for 30 minutes, a solution of 440 mg. of phenyl disulfide in 1 ml. of tetrahydrofuran is added slowly to the reaction mixture. After stirring for 10 minutes at 78° C., the reaction mixture is allowed to warm to room temperature. The mixture is then added to water, and the product is extracted into ethyl acetate. The organic layer is washed with dilute sodium hydroxide solution, then water, then dilute hydrochloric acid, and finally with saturated sodium chloride solution. The solution is dried over calcium sulfate and is then concentrated to the crude solid product. Elution through 30 g. of silica gel with increasing amounts of ethyl acetate in hexane affords the 2-phenylthio derivative as an apparent mixture of two isomers. This material, suspended in 5 ml. of 20% aqueous methanol is treated with a solution of 225 mg. of sodium metaperiodate in 2 ml. of water. After stirring 16 hours, the reaction mixture is diluted with water and extracted with methylene chloride. The organic layer is washed with water, dried, and concentrated to leave the crude sulfoxide. A solution of this material in 5 ml. of toluene is refluxed for 30 minutes. The solvent is removed and the residue is chromatographed on 20 g. of silica gel eluting with increasing amounts of ethyl acetate in ether. The final product crystallizes on trituration with ether.

EXAMPLE 11

17β-N,N-diethylcarbamoyl-4-aza-5α-androst-1-en-3-one

A solution of 291 mg. of 17β-N,N-diethylcarbamoyl-4-aza-5α-androstan-3-one in 3 ml. of methylene chloride is added at 0° C. to a solution of 117 mg. of trimethyloxonium fluoroborate in methylene chloride. The mixture is then stirred at 0° C. for 6 hours and then is treated with 125 mg. of 1,5 diazobicyclo [5,4,0] undec-5-ene. Stirring is continued for 2 hours and the reaction mixture is diluted with anhydrous ether. The organic solution is separated from the residue and concentrated under reduced pressure to leave the crude lactim ether. This material is then converted to the corresponding Δ1 compound in accordance with the procedures described above in Example 15.

EXAMPLE 12

17β-N,N-diethylcarbamoyl-4-methyl-4-aza-5α-androstan-3-one

A. 17B-N,N-diethylcarbamoyl-4-aza-5-androsten-3-one

A solution of 90 g. of 17β-N,N-diethylcarbamoyl-5-oxo-3,5-secoandrostan-3-oic acid in 600 ml. of dry ethanol saturated with ammonia at 0° C. is heated in a bomb at 180° C. for 8 hours. After cooling, the somewhat brownish solution is allowed to evaporate and is concentrated to dryness, yielding a yellowish foam, which upon trituration with cyclohexane gives 17β-N,N-diethylcarbamoyl-4-aza-5-androsten-3-one.

B. 17β-N,N-diethylcarbamoyl-4-aza-5α-androstan-3-one

A solution of 25 g. of the compound prepared in Step A. above in 140 ml. of glacial acetic acid is hydrogenated at 40 psi and room temperature in the presence of 2.5 g. of platinum oxide and 0.1 ml. of perchloric acid. Upon uptake of the theoretical amount of hydrogen required, after about 6 hours, the residue is filtered and the filtrate concentrated to dryness. The residue is dissolved in 100 ml. of methylene chloride, washed twice with 50 ml. of a saturated sodium chloride solution and then with 50 ml. of a 5% sodium bicarbonate solution. After drying over magnesium sulfate, the solution is concentrated to dryness and the residual oil is dissolved in ethanol, filtered with activated charcoal, and water is added slowly until crystallization begins. After cooling at 5° C., the crystalline product is filtered off, washed with water and dried.

C. 17β-N,N-diethylcarbamoyl-4-methyl-4-aza-5α-androstan-3-one

A solution of 36 g. of the product of Step B. above in 700 ml. of toluene is treated with a slurry of 5.4 g. of 50% sodium hydride emulsion in 20 ml. of toluene, followed by the slow addition of 16 g. of methyl iodide. After stirring for 3 hours at room temperature, any unreacted sodium hydride is quenched with 5 ml. of ethanol in 25 ml. of toluene, followed by 1 liter of water. The product is extracted three times with 500 ml. of toluene each time, and the combined extracts are then washed three times with water, dried over magnesium sulfate, and the filtrate concentrated to dryness. The pure 17β-N,N-diethylcarbamoyl-4-methyl-4-aza-5α-androstan-3-one is obtained by crystallization from ethanol and water.

EXAMPLE 13

17β-N,N-diethylcarbamoyl-4-methyl-4-aza-5α-androstan-3-one

A slurry of 20 g. of 17β-N,N-diethylcarbamoyl-5-oxo-3,5-secoandrostan-3-oic acid in 120 ml. of ethanol is saturated with methylamine gas and added to an autoclave containing 2 g. of pre-reduced platinum oxide in 25 ml. of ethanol. The mixture is then reduced for 6 hours at 40 psi and 40° C. The autoclave is then vented, resealed, and heated at 180° C. for 8 hours to effect ring closure. The mixture is filtered and the filtrate concentrated in vacuo to dryness. The residue is crystallized from ether. Filtration and drying give substantially pure 17β-N,N-diethylcarbamoyl-4-methyl-4-aza-5α-androstan-3-one.

EXAMPLE 14

17β-N,N-diethylcarbamoyl-4-methyl-4-aza-5α-androstan-3-one

A. 5-oxo-3,5-secoandrostan-3,17β-dioic acid

To 31.6 g. (0.1 mole) of 17-carboxy-4-androstan-3-one in 1100 ml. of tert-butanol is added a solution of 27.6 g. of potassium carbonate in 150 ml. of water. A solution of 148 g. of sodium metaperiodate in 925 ml. of water is prepared and 185 ml. of this solution is added in one portion, with the remainder added at a rate of 37 ml. per minute. A 1.6% aqueous solution of potassium permanganate (18.5 ml.) is added in portion with the original charge of periodate solution, and then added as needed to maintain a pink-colored reaction mixture. During the addition period the temperature is maintained at 35° C. After stirring an additional 2 hours, the mixture is filtered and sufficient sodium bisulfite is added to discharge the pink color. The mixture is then concentrated to half-volume, acidified, and extracted into ethyl acetate. The solution is then concentrated to give the product 5-oxo-3,5-secoandrostan-3,17β-dioic acid of sufficient purity to be used in the next step.

B. 17-carboxy-4-methyl-4-aza-5-androsten-3-one

A slurry of 20 g. of the product of Step A above is 150 ml. of ethanol is saturated with methylamine gas and the mixture is transferred to an autoclave and heated at 180° C. for 8 hours. The mixture is then cooled and concentrated to dryness. The residue is slurried in water, acidified, and filtered to give the 17-carboxy-4-methyl-4-aza-5-androstan-3-one.

C. 17-carboxy-4-methyl-4-aza-5α-androstan-3-one

A solution of 10.0 g. of the product of Step B above in 40 ml. of glacial acetic acid and 0.05 ml. of perchloric acid is hydrogenated at 40 psi at room temperature with 1.0 g. of platinum oxide as catalyst. After hydrogen uptake ceases, the catalyst is filtered off and the filtrate is concentrated to near dryness. The residue is dissolved in dilute aqueous sodium bicarbonate, treated with 1.0 g. of activated charcoal, filtered, and the filtrate acidified. The product is filtered and dried.

D. 17β-N,N-diethylcarbamoyl-4-methyl-4-aza-5α-androstan-3-one 5.0 g. of the product of Step C above is treated with an equivalent of 1 N sodium hydroxide solution. The mixture is stirred overnight, then lyophilized and dried over phosphorous pentoxide in vacuuo. The sodium salt of the 17-carboxy compound thus formed is suspended in 100 ml. of dry toluene. The slurry is cooled to 15° C. and 3 ml. of oxalyl chloride is added dropwise at 15° C. The mixture is stirred for an additional twenty minutes and then concentrated to dryness. Thirty ml. of tetrahydrofuran is then added and this mixture is added with cooling and stirring to a solution of 6 ml. of diethylamine in 30 ml. of tetrahydrofuran. The mixture is stirred for one hour and poured into 1 liter of water. The product is extracted into chloroform, washed successively with dilute sodium bicarbonate solution and saturated sodium chloride solution, and then dried over magnesium sulfate. The chloroform extract is distilled in vacuuo and the residue crystallized from ether to give substantially pure 17β-N,N-diethylcarbamoyl-4-methyl-4-aza-5α-androstan-3-one.

EXAMPLE 15

17β-N,N-diethylcarbamoyl-4-methyl-4-aza-5α-androstan-3-one

A. (3β-hydroxypregn-5-en-20-one-21-yl) pyridinum iodide

To 2 l. of pyridine was added 1 kg. (3.16 moles) of pregnenolone, and the mixture was heated to 90°–95° C. with moderate stirring, after which the pregnenolone was all dissolved. To the mixture was then cautiously added a total of 866.1 g. (3.41 moles) of iodine over 15–20 minutes, and the reaction mixture temperature was observed to rise to 120° C. The mixture was stirred for 1 hour with the temperature at 100° C. or above, after which it was allowed to cool gradually for 1 hour and was then placed in a cool water bath to bring it to room temperature. The product was collected on a medium porosity silica gel funnel and was found to be rubbery and gel-like. Filtration was aided by addition of pyridine, and the filtered product was washed 6 times with 300 ml. of pyridine, and then 6 times with 300 ml. of ether, followed by air drying. The product, having a m.p. of 228°–230° C., was obtained in 99% yield (1635.8 g.).

B. methyl 5-androsten-3β-ol-17βcarboxylate

To a flask there was charged 2.7 kg. (5.177 moles) of (3β-hydroxypregn-5-en-20-one-21-yl) pyridinium iodide, 13.5 l. of methanol, and 900 g. of sodium methoxide. The mixture was refluxed for 1 hour, after which it was allowed to cool to about 53° C., and then quenched by adding 24 l. of ice and 2 l. of water, to bring the reaction mixture temperature to 5° C. The mixture was then neutralized by adding 2100 ml. of 1:1 hydrochloric acid and water, giving a pH of 6–7. The mixture was aged for 45 minutes and then collected on a Lapp funnel, after which it was washed well with cold water, until most of the color was washed out. The product was dried briefly on the funnel and then transferred to two glass trays for drying in an air oven at 50° C. overnight. The yield of product was 83.6% (1440 g.).

C. methyl 4-androsten-3-one-17$\beta$-carboxylate

To a flask there was charged 160.0 g. of methyl 5-androsten-3$\beta$-ol-17$\beta$-carboxylate, 2.4 l. of sieve dried toluene, and 680 ml. of cyclohexanone. The mixture was heated to reflux and any water present was removed by azeotroping for 15 minutes, i.e., until the distillate was clear. Then, 88 g. of aluminum isopropoxide in 320 ml. of dry toluene was added all at once as a slurry. The reaction mixture was refluxed while removing about 800 ml. of toluene over 1 hour. The mixture was then cooled to 25° C. and 40 g. of diatomaceous earch was added, followed by 80 ml. of water. The mixture was stirred for 10 minutes and filtered through diatamaceous earth, then washed three times with 300 ml. of toluence. The filtrate was concentrated to near dryness, then chilled on an ice bath. The product crystallized out, was aged at 0°–5° C., collected, and washed with cold hexane, then dried in vacuo. The yield of product was 83.6% (133 g.), which had a m.p. of 130°–132° C.

D. 4-androsten-3-one-17$\beta$-carboxylic acid

To 2.462 kg. of methyl 4-androsten-3-one-17$\beta$-carboxylate in 24.6 l of methanol was added 1.23 kg. of potassium hydroxide in 4.9 l. of water. The reaction mixture was refluxed under nitrogen for 6 hours, and then allowed to cool to room temperature overnight. The mixture was acidified with 3200 ml. of 6 N hydrochloric acid. Most of the product crystallized as fine crystals. Then, 14 l. of water was added in a stream over 30 minutes, which precipitated all of the product. The mixture was aged with stirring for 4 hours at 30° C. The mixture was filtered on a cap funnel and washed with water until the wash water showed neutral. The product was dried in an oven at 50° C. overnight. The product, having a m.p. of 245°–248° C., was obtained in 98% yield (2.313 g.).

E. 17$\beta$-N,N-diethylcarbamoyl-4-androsten-3-one

To a flask were charged 700 g. of 4-androsten-3-one-17$\beta$-carboxylic acid and 11.6 l. of toluene dried by azeotroping. To the mixture was added 226 ml. of sieve-dried pyridine, after which there was cautiously added 250 ml. of oxalyl chloride in 250 ml. of dried toluene over 20 minutes. The reaction mixture was aged for 1 hour at room temperature, and then chilled to 10° C. There was then added sieve-dried diethyl amine in equal volume of dry toluene in sufficient amount to obtain a persistant alkaline pH. About 2.4 l. of solution were required. The reaction mixture was aged for 30 minutes and then quenched by addition of 16 l. of ice water. The resulting layers were separated and the aqueous layer was extracted three times with 4 l. of ethyl acetate. The combined organic layers were washed with 8 l. of water and hydrochloric acid to make the batch acidic (pH 3), and then with 8 l. of water alone, and finally with 8 l. of saturated sodium chloride solution. The batch was dried over sodium sulfate and then concentrated to a small volume of 3 to 4 l. on a large rotating evaporator. Then, 4 l. of hexane were added to the batch and it was chilled to 0°–5° for 1 hour. The product was collected and washed three times with small amounts of cold hexane, then dried in an air oven overnight at 40°–50° C. The product, having a m.p. of 119°–121° C., was obtained in 75% yield (616.5 g.).

F. 17$\beta$-N,N-diethylcarbamoyl-5-oxo-3,5-secoandrostan-3-oic acid

To a flask was charged 600 g. of 17$\beta$-N,N-diethylcarbamoyl-4-androsten-3-one and 18 l. of tertbutanol in which it was dissolved. Then, a solution of 258 g. of sodium carbonate in 1200 ml. of water was added. Next, a solution of 2.4 kg. of sodium periodate in 18 l. of water was added over a period of 1.5 hours, while adding 1340 ml. of 2% potassium permanganate over the same period of time to maintain the pink color of the reaction mixture. The temperature was maintained between 25° and 40° C. during the addition period. The mixture was aged for 2 hours, filtered, and the cake washed with water. The tert-butanol was concentrated off until only aqueous solution was left, and this was then cooled to 10° C. and acidified with 110 ml. of 50% sulfuric acid (pH 3). The aqueous solution was extracted 3 times with 6 l. of ethyl acetate. The combined ethyl acetate washings were washed with 4 l. of 5% sodium bisulfate solution, then twice with 4 l. of saturated sodium chloride solution. The combined extracts were dried over sodium sulfate and concentrated to 1.5 l., then brought to the boiling point and aged for 2 hours at 5°–10° C. The batch was filtered and the filter cake washed with ethyl acetate. A yield of 77% (488 g.) of product having a m.p. of 205°–208° C. was obtained.

G. 17$\beta$-N,N-diethylcarbamoyl-4-methyl-4-aza-5-androsten-3-one

Into a graduated cylinder maintained in a dry ice bath there was condensed 200 ml. of methylamine, which was then added with stirring to 1250 ml. of ethylene glycol at room temperature. A 16% volume increase was observed. The methylamine/ethylene glycol solution was added to 250 g. of 17$\beta$-N,N-diethylcarbamoyl-5-oxo-3,5-secoandrostan-3-oic acid in a 3 l. flask. Solution was obtained in a few minutes. The reaction mixture was heated to 110° C. over 40 minutes, and the heating was continued at the rate of 2° per minute until the temperature reached 180° C. Then, the heat was removed. The total elapsed heating time as 70 minutes. The reaction mixture was quenched into 10 l. of water, and a milky solution resulted which was extracted 5 times with 2 l. of dichloromethane. The combined organic extracts were washed with 4 l. of water acidified with concentrated hydrochloric acid, 4 l. of 5% sodium bicarbonate solution, and 3 times with 4 l. of water. The combined organic extracts were then dried over sodium sulfate and treated with 50 g. of silicon dioxide, then concentrated to dryness. The residue was dissolved in a solution of 750 mg. of cyclohexanone in 750 ml. of n-hexane, and then aged with stirring at room temperature overnight. The product was filtered, washed with n-hexane, and dried in vacuo. The final yield of product having a m.p. of 115°–118° C. was 91% (226 g.).

H. 17$\beta$-N,N-diethylcarbamoyl-4-methyl-4-aza-5$\alpha$-androstan-3-one

To a flask there was charged 150 g. of 17$\beta$-N,N-diethylcarbamoyl-4-methyl-4-aza-5-androsten-3-one and 750 ml. of glacial acetic acid, and the mixture was heated to 60° C. under nitrogen at 45 psi for 4 hours. The product was filtered, the filter cake washed with dichloromethane, and the filtrate concentrated to dryness. The residue was dissolved in 750 ml. of dichloromethane and washed twice with 500 ml. of 1 N sulfuric acid, once with 500 ml. of water, once with 500 ml. of saturated sodium bicarbonate solution, and once with saturated sodium chloride solution. The solution was dried over magnesium sulfate and treated with 15 g. of activated charcoal, filtered through a pad of 75 g. of silicon dioxide. The filter cake was washed with 1 l. of dichloromethane and concentrated to dryness. The residue was dissolved in 450 ml. of ethyl acetate and then aged 1 hour at room temperature and one hour in an ice bath. The product was filtered and washed with 50 ml. of ethyl acetate, then 100 ml. of n-hexane, and dried. The filtrate was concentrated to dryness, dissolved in 100 ml. of ethyl acetate, aged 2 hours at room temperature, filtered, and washed with 15 ml. of ethyl acetate and 100 ml. of n-hexane. The yield of product having a m.p. of 172°–174° C. was 76.6% (115 g.).

EXAMPLE 16

17β-N,N-diethylcarbamoyl-4-methyl-4-aza-5α-androstan-3-one

A. 17β-carbamoyl-4-methyl-4-aza-5α-androstan-3-one

To a toluene solution of 17β-carbonylchloro-4-methyl-4-aza-5α-androstan-3-one is added a solution of ammonia in tetrahydrofuran, and the reaction mixture is stirred for 2 hours at room temperature. Addition of water and extraction with ethyl acetate gives the intermediate amide.

B. 17β-N,N-diethylcarbamoyl-4-methyl-4-aza-5α-androstan-3-one

The product of step A is ethylated with ethyl bromide in the presence of an equimolar amount of sodium hydride in a toluene solution. Use of two moles of the ethyl bromide per mole of product of step A gives the final product.

EXAMPLE 17

17β-N,N-diethylcarbamoyl-4-methyl-4-aza-5α-androstan-3-one

A. 17β-N-ethylcarbamoyl-4-methyl-4-aza-5α-androstan-3-one

To a toluene solution of 17β-carbonylchloro-4-methyl-4-aza-5α-androstan-3-one is added a solution of monoethylamine in tetrahydrofuran, and the reaction mixture is stirred for 2 hours at room temperature. Addition of water and extraction with ethyl acetate gives the 17β-N-ethylcarbamoyl product.

B. 17β-N,N-diethylcarbamoyl-4-methyl-4-aza-5α-androstan-3-one

The product of step A is ethylated using ethyl bromide and sodium hydride in the same manner as described in step B of Example 16, but using one mole of ethyl bromide per mole of the product of step A.

EXAMPLE 18

N-methyl-N-[17β-(N',N'-diethylcarbamoyl)-4-aza-4-methyl-5α-androst-3-en-3-yl]amine hydrochloride To a mixture of 160 mg. of trimethyloxonium fluoroborate in 3 ml. of methylene chloride is added at 0° C. a solution of 375 mg. of 17β-N,N-diethylcarbamoyl-4-methyl-4-aza-5α-androstan-3-one in 3 ml. of methylene chloride. After stirring at 0°–5° C. for 6 hours the mixture is allowed to stand at room temperature overnight. Diazabicyclo [5.4.0.] undec-5-ene (160 mg.) is added and the organic layer is diluted with anhydrous ether. The solid residue is removed by centrifugation and the organic layer is concentrated to dryness to leave the Δ²-lactimino methyl ether. A mixture of this material with 1.0 g. of methylamine in 5 ml. of toluene is heated in a sealed tube at 100° C. for 24 hours. After cooling, the tube is opened and the solution is concentrated to dryness under a nitrogen stream. The residue is dissolved in 8 ml. of ethyl acetate and a slow stream of anhydrous hydrogen chloride is introduced at 0° C. The precipitated product, which is removed by centrifugation, washed twice with ether and dried in vacuo, is N-methyl-N-[17β-(N',N'-diethylcarbamoyl)-4-aza-4-methyl-5α-androstan-3-en-3-yl]amine hydrochloride.

What is claimed is:

1. A method of preparing the compound of the formula:

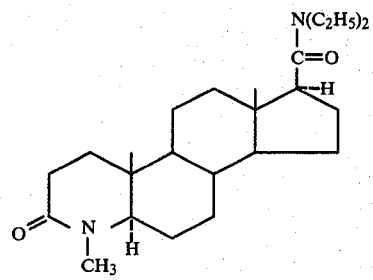

comprising the steps of (1) treating pregnenolone with iodine and pyridine to form the corresponding 20-pyridinium iodide derivative of pregnenolone;

(2) methanolyzing the product of step (1) to form the methyl ester of 17-carboxy androstenol;

(3) treating the product of step (2) with aluminum isopropoxide and cyclohexanone to form methyl-4-androsten-3-one-17-carboxylate;

(4) hydrolyzing the product of step (3) to form the corresponding 17-acid compound;

(5) treating the product of step (4) with an oxalyl chloride: pyridine complex to form the corresponding 17-acid chloride compound;

(6) treating the product of step (5) in situ with diethylamine to form 17β-N,N-diethylcarbamoyl-4-androsten-3-one;

(7) oxidizing the product of step (6) with sodium periodate and potassium permanganate in a tert-butanol: water solvent system to form the corresponding 5-oxo-3,5-secoandrostan-3-oic acid compound;

(8) treating the product of step (7) with methylamine in ethylene glycol to form 17β-N,N-diethylcarbamoyl-4-methyl-4-aza-5-androsten-3-one;

(9) hydrogenating the product of step (8) by treating it with hydrogen under catalytic conditions to form the final product, 17β-N,N-diethylcarbamoyl-4-methyl-4-aza-5α-androstan-3-one.

2. A method of preparing the compound of the formula:

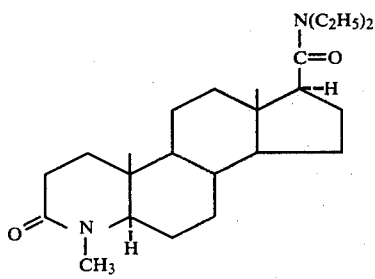

comprising the steps of (1) treating 4-androsten-3-one-17β-carboxylic acid with an oxalyl chloride: pyridine complex to form the corresponding 17-acid chloride;
(2) treating the product of step (1) in situ with diethylamine to form 17β-N,N-diethylcarbamoyl-4-androsten-3-one;
(3) oxidizing the product of step (2) with sodium periodate and potassium permangenate in a tert-butanol: water solvent system to form the corresponding 5-oxo-3,5-seconandrostan-3-oic acid compound;
(4) treating the product of step (3) with methylamine in ethylene glycol to form 17β-N,N-diethylcarbamoyl-4-methyl-4-aza-5-androsten-3-one;
(5) hydrogenating the product of step (4) by treating it with hydrogen under catalytic conditions to form the final product, 17β-N,N-diethylcarbamoyl-4-methyl-4-aza-5α-androstan-3-one.

* * * * *